(12) United States Patent
Myers

(10) Patent No.: US 9,675,504 B2
(45) Date of Patent: Jun. 13, 2017

(54) DISPOSABLE WATER RESISTANT PROTECTIVE COVER CAST AND WOUND SITES

(71) Applicant: Lisa Ann Myers, Methuen, MA (US)

(72) Inventor: Lisa Ann Myers, Methuen, MA (US)

( * ) Notice: Subject to any disclaimer, the term of this patent is extended or adjusted under 35 U.S.C. 154(b) by 296 days.

(21) Appl. No.: 14/121,155

(22) Filed: Aug. 6, 2014

(65) Prior Publication Data
US 2016/0038354 A1   Feb. 11, 2016

Related U.S. Application Data

(60) Provisional application No. 61/870,922, filed on Aug. 28, 2013.

(51) Int. Cl.
A61F 5/00      (2006.01)
A61F 15/00     (2006.01)
A61F 13/04     (2006.01)

(52) U.S. Cl.
CPC .......... A61F 15/004 (2013.01); A61F 13/041 (2013.01); A61F 2210/0076 (2013.01); A61F 2220/005 (2013.01)

(58) Field of Classification Search
CPC ......... A61F 15/00; A61F 15/004; A61F 13/00
See application file for complete search history.

(56) References Cited

U.S. PATENT DOCUMENTS

| 3,298,507 | A | * | 1/1967 | Micciche | A46B 5/04 15/104.94 |
| 8,168,848 | B2 | * | 5/2012 | Lockwood | A61F 13/0203 602/41 |
| 8,372,049 | B2 | * | 2/2013 | Jaeb | A61M 1/0088 604/313 |
| 9,174,034 | B2 | * | 11/2015 | Loori | A61M 35/00 |
| 9,198,801 | B2 | * | 12/2015 | Weston | A61M 1/0001 |
| 2005/0283050 | A1 | * | 12/2005 | Gundlapalli | A61B 17/0293 600/208 |
| 2007/0129707 | A1 | * | 6/2007 | Blott | A61F 13/00068 604/543 |
| 2008/0033334 | A1 | * | 2/2008 | Gurtner | A61L 15/42 602/50 |
| 2010/0121286 | A1 | * | 5/2010 | Locke | A61B 17/085 604/319 |

* cited by examiner

Primary Examiner — Kristen Matter
(74) Attorney, Agent, or Firm — Don Halgren

(57) ABSTRACT

A protective cover for use as a liquid barrier includes an enclosure having a supported front sheet and a back sheet. The enclosure is made of a flexible, liquid impervious material, the back face having a periphery in the interior of the back face that defines an opening; and an adhesive layer extending along the periphery of the back face for securing the periphery onto a body part, wherein the periphery is positioned and sized to define an opening that can accommodate a body part to be shielded from liquid.

14 Claims, 4 Drawing Sheets

DISPOSABLE WATER RESISTANT PROTECTIVE COVER CAST AND WOUND SITES

FIELD OF THE INVENTION

The present invention relates to barriers for inhibiting liquid contact with a wound site, cast or other body site. In particular, the barriers may be used to protect parts of a person's body that are, for example, covered with a dressing or a cast from becoming wet when showering or bathing, and is based upon Provisional Application No. 61/870,922, filed 8 Aug. 2013, incorporated herewith.

BACKGROUND

Generally, when a person having a wound with a medical dressing or a cast is to shower or bath, a water impervious barrier such as plastic sheeting is used to cover the area. A typical form of dressing is the use of a garbage bag or plastic grocery bag, tied, rubber-banded or taped at the opening in an attempt to create a waterproof covering. Tape is often used to seal the edges in an attempt to make the area airtight or waterproof. Such arrangements tend to leak, particularly when the wound is at a location where bending or movement of the body occurs.
Frequently, these methods are ineffective at best and potentially harmful to the wearer at worst and render the item useless after a single use.

Liquid barriers have been described that use elastic bands to create a water barrier. See, e.g., U.S. Pat. No. 7,290,290. Often, it is used as a strip, wrapped around the limb, similar to the use of a tourniquet. In addition to not always forming a water tight seal, this approach to using elastic could be harmful to the wearer if overtightened or left on too long, particularly by those wearers with diseases, such as diabetes, who have circulatory problems.

Liquid barriers also have been described that use adhesive strips to form a watertight seal. See, e.g., U.S. Pat. No. 5,152,282. The barrier is a single sheet open on all sides, which may allow water to flow under the sheet and to interfere with the adhesive, thereby causing water to come in contact with the wound.

SUMMARY OF THE INVENTION

In one aspect, a disposable water resistant protective cover is described. The device is particularly useful as protective sleeves for bodily extremities and or wound sites located on the torso. The device uses a water resistant material and a water tight seal to exclude moisture and keep body parts dry. The device uses an adhesive sealing strip located near the opening allowing enclosure of bodily extremities and or the torso to be protected. One of the features of this device is that wounds and or surgical dressings located on the torso can be covered and protected from moisture. Traditional waterproof coverings cannot accommodate wounds or surgical incisions located on the torso and provide little protection from water.

The disposable water resistant protective cover is intended to be disposable and can be discarded after use. This is preferable to the same cover being reused, as repeated use of a device that is used in water runs the risk of harboring mildew, bacteria and other microorganisms that could be harmful to the user.

In one aspect, a protective cover for use as a liquid barrier has an enclosure including a front sheet and a back sheet, the enclosure made of a flexible, liquid impervious material, the back sheet having a periphery in the interior of the back sheet that defines an opening; and an adhesive layer extending along an inner surface of the periphery of the back sheet for securing the periphery onto a body part, wherein the periphery is positioned and sized to define an opening that can accommodate a body part to be shielded from liquid.

In one or more embodiments, the front and back sheets are sealed along their edges with a liquid impervious seal.

In one or more embodiments, the front sheet is integral with the back sheet along two opposing sides, thereby forming a tube and the opposing edges are sealed with a liquid impervious seal.

In one or more embodiments, the protective cover further includes an adhesive backing disposed over the adhesive layer.

In one or more embodiments, the protective cover further includes a moisture indicator disposed in the interior of the enclosure.

In one or more embodiments, the protective cover further includes an antimicrobial agent disposed in the interior of the enclosure.

In one or more embodiments, the front face is capable of being spaced apart from the back face when in use.

In one or more embodiments, the cover is attachable to the torso of a body.

In one or more embodiments, the cover is attachable to a joint of a body.

In one or more embodiments, the cover comprises a gusset along at least one edge that joins the front and back sheets.

In another aspect, a protective sleeve for use as a liquid barrier includes an enclosure made of a flexible, liquid impervious material having an opening dimensioned for accommodating a body part; an adhesive layer extending along a periphery extending along the opening of the enclosure; an adhesive backing disposed over the adhesive layer; and a moisture indicator disposed in the interior of the enclosure.

In one or more embodiments, the protective cover further includes an antimicrobial agent disposed in the interior of the enclosure.

BRIEF DESCRIPTION OF THE DRAWINGS

The following figures are provided for the purpose of illustration only and are not intended to be limiting.

DETAILED DESCRIPTION OF THE INVENTION

The current invention provides a disposable, affordable design that will offer protection for the wearer from harmful or damaging fluids, moisture or other contaminants. This invention can be used for the protection of casts, IVs, surgery sites, burns, rashes, dressings, wounds, amputations, vaccines, tattoos, etc., but not limited to medical uses.

The various aspects of the invention can be prepared from flexible polymer films that have a thickness and a durability that provides ease of movement by the user, and toughness sufficient to prevent tearing or other damage during use. Exemplary flexible polymer films include those made of low density polyethylene or polypropylene having for example a thickness in the range of 0.001-0.050 mils and preferably about 0.002 mils. The polymer film can be cut into any desired shape and can be made air tight, for example, by heat sealing the edges.

Figure 1:
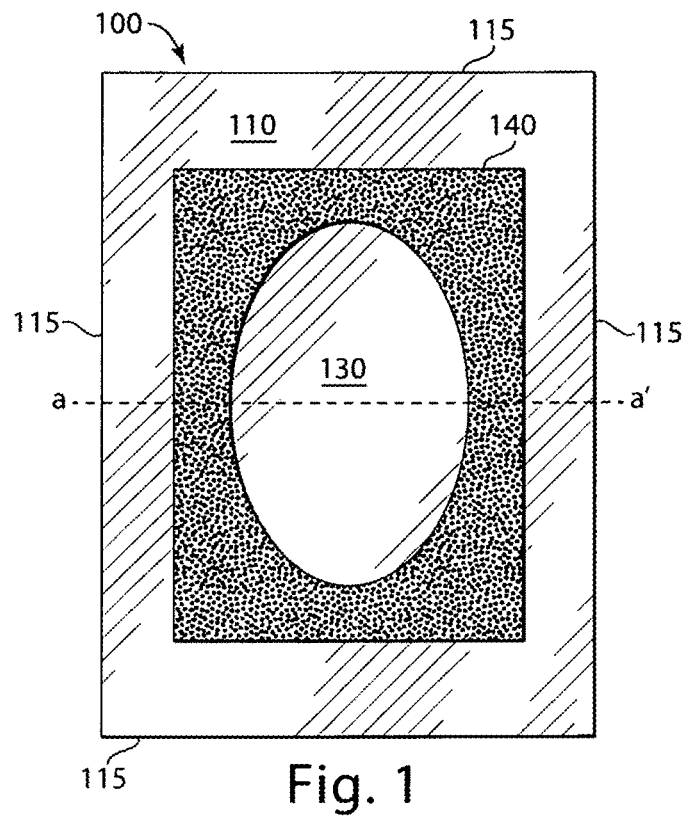
FIG. 1 depicts a plan view of a water impervious protective cover according to one or more embodiments showing the side to be against a user body part, such as a torso or knee.
Figure 2:
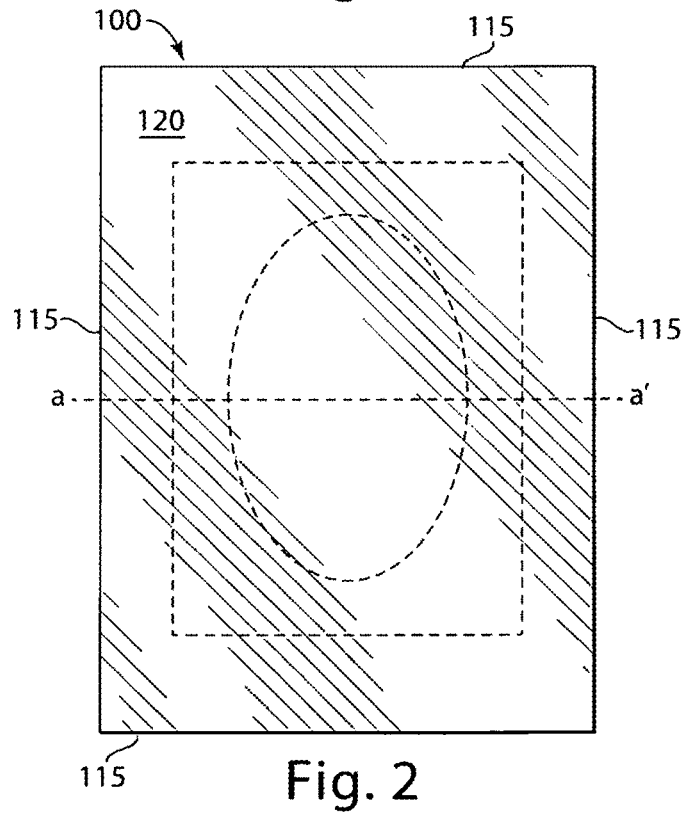
FIG. 2 depicts a plan view of the water impervious protective cover of FIG. 1 showing the side facing away from the user; dashed lines indicate features viewable through the thickness of a transparent plastic sheet.
Figure 3:
FIG. 3 is a cross sectional view of the a water impervious protective cover of FIGS. 1 and 2 along line a-a'.

FIGS. 1-3 depict views of one embodiment of water impervious protective cover 100 that can be applied to a body surface of a user. FIG. 1 is a plan view of the protective cover 100 from the side contacting the user, while FIG. 2 is a plan view of the protective cover 100 from the side facing away from the user. Dashed lines shown in FIG. 2 indicate features viewable through the thickness of a transparent plastic sheet. FIG. 3 is a cross-sectional view as viewed along line a-a' shown in FIGS. 1 and 2. Like numbering is used to indicate like elements in all figures.

The protective cover includes a first flexible sheet 110 and a second flexible sheet 120 that are joined along the edges in a water tight seal. The sheets 110 and 120 can optionally be transparent, so that it is possible to view the interior of the protective cover. Flexible sheet 110 contains an opening 130 that provides access to the interior of the protective cover. The protective cover also includes an adhesive layer 140 that is secured around opening 130. The adhesive layer is relative flexible and bendable. The adhesive can be formed of non-allergenic adhesives, as are known in the art. The adhesive can be selected from a class of adhesives that are non-permanent and that cause little or no pain to the user upon removal. Exemplary adhesives are of medical grade or hypoallergenic and are adhesive to the polymer sheets used as the protective layer. Exemplary adhesives include double sided Red Adhesive Pouch tabbing tape, ME D 3044 (available from Universal Tape). The adhesive layer also has an adhesive backing 150 made of nonstick or low stick material. The adhesive backing 150 protects the adhesive layer during storage, but can be readily removed to expose the adhesive layer in preparation for use.

In use, the adhesive backing 150 is removed to expose the adhesive layer and the protective cover 100 is applied to an area of the body by pressing the exposed adhesive layer onto the body, starting first at one edge or side and moving around the opening. In some embodiments, the protective cover can have more than one adhesive backing, each covering only a portion of the adhesive layer. Such backings can be removed one at a time, so that only a portion of the adhesive layer is exposed at any one time.

Figure 4:
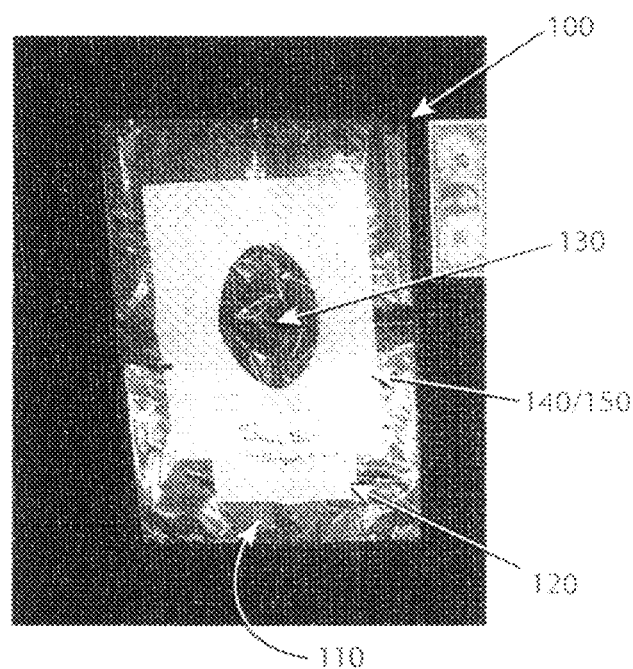
FIG. 4 is a photograph of an exemplary protective wound dressing according to one or more embodiments.
Figure 5:
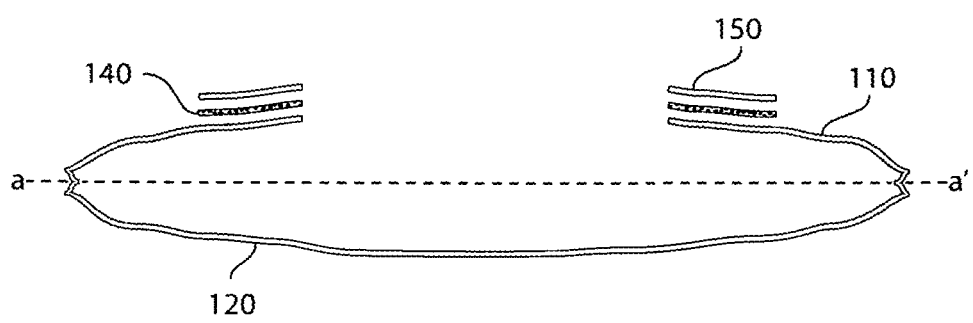
FIG. 5 is a schematic illustration of a water impervious protective including gusseted edges to provide additional freedom of movement.
Figure 6:
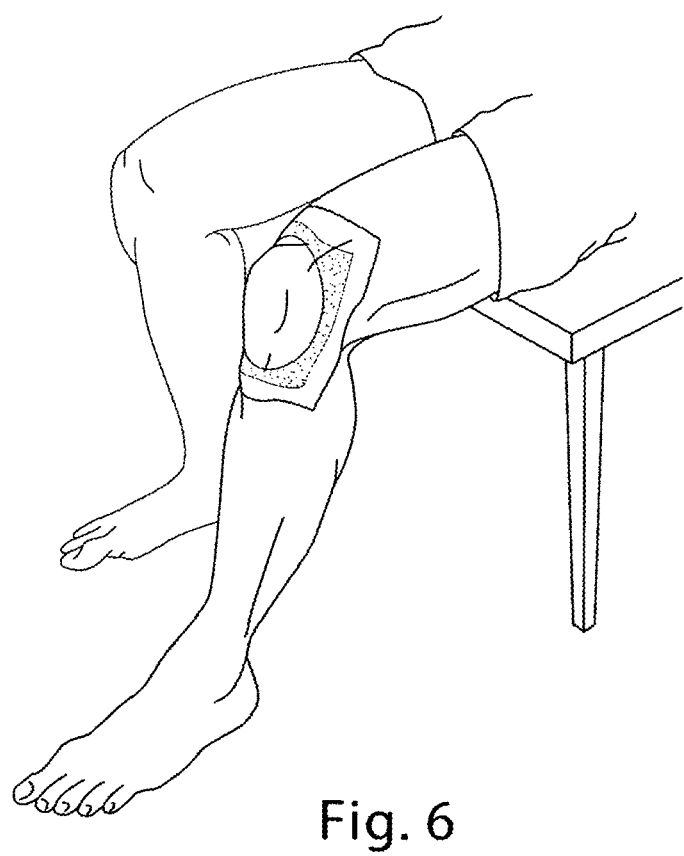
FIG. 6 depicts a method of use of the water impervious protective coating according to one or more embodiments, in which the barrier is applied to a human knee.

FIG. 4 is a photograph of an exemplary protective wound dressing according to one or more embodiments. The opening is of a size that covers wound or wound dressing. The protective cover can be provided having an opening in a range of sizes ranging from small, e.g., 1 cm×1 cm, to large, e.g., 10 cm×10 cm, or for example having a surface area of 1 $cm^2$ to 100 $cm^2$, although larger or smaller areas are contemplated. In addition, the flexible cover may be sufficiently thin that it is possible to enlarge the opening by cutting. Because the protective covering is made of two layers that are separable from one another, they can be adjusted to prevent contact of the wound with plastic sheeting. In addition, the two polymer layers allow for movement, e.g., bending, of the protected body part without imposing strain on the protective cover. In one or more embodiments, the protective cover can include gusseted edges, as is shown in FIG. 5, to provide additional freedom of movement for the user. FIG. 6 is an illustration of the protective cover applied to the user's knee. The adhesive layer is sufficient wide and flexible to provide a sealing contact that encircles and seals the knee. However, the protective cover can be adjusted to be spaced apart from the knee itself, so that the wound does not come into direct contact with the cover and to provide enough room for flexing and bending of the knee.

Figure 7:
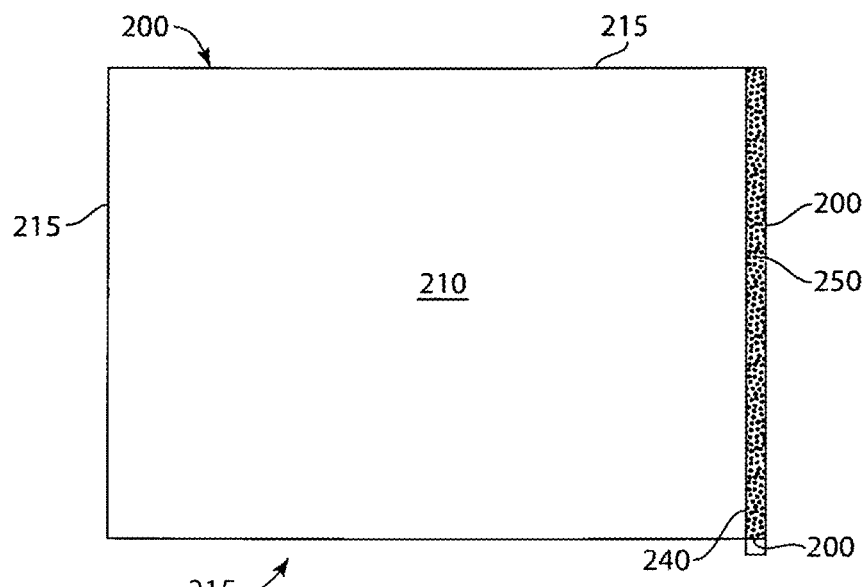
FIG. 7 depicts a water impervious protective cover according to one or more embodiments.

In another aspect of the invention, the protective cover is in the form of a sleeve 200 that is made up of materials similar to the flexible sheeting 110 and 120 (hereinafter referred to as the "protective sleeve"), as is illustrated in FIG. 7. One edge is left unsealed to provide an opening for the entrance of a limb or other body part. The protective sleeve includes a first flexible sheet 210 and a second flexible sheet 220 (not shown) that are joined at the edges 215 in a water tight seal along three sides. The fourth side 230 remains open to allow it to receive a limb of a person. The sheets 210 and 220 can optionally be transparent, so that it is possible to view the interior of the protective cover.

The protective sleeve also includes an adhesive layer 240 that is secured around the opening 230 along one edge of sleeve. The adhesive layer is relative flexible and bendable. The adhesive can be formed of non-allergenic adhesives, as are known in the art. The adhesive can be selected from a class of adhesives that are non-permanent and that cause little or no pain to the user upon removal. The adhesive layer also has an adhesive backing 250 made of nonstick or low stick material. The adhesive backing 250 protects the adhesive layer during storage, but can be readily removed to expose the adhesive layer in preparation for use. For ease of use, the adhesive backing can include a tab 260 for grasping and removal of the backing.

In use, a limb of the user is inserted into the open end of protective sleeve 200. A portion of the adhesive backing is removed (or the adhesive backing can be provided in multiple sections for this purpose), and the exposed adhesive layer is contacted with the user's limb. Additional adhesive backing is removed to continue to contact the limb, until an adhesive seal around the limb has been formed. If the opening is larger than the limb, the opposing excessive edges can be pressed together to complete the seal.

Figure 8:
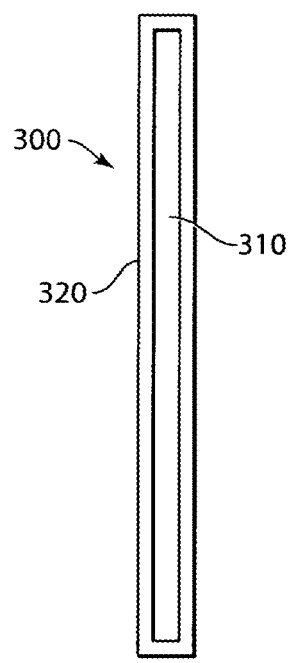
FIG. 8 is a schematic illustration of a water impervious strip for use with the water impervious protective cover of FIG. 7.

In order to assure that the seal is completely watertight, and addition protective strip 300 can be applied over the seal, as shown in FIG. 8. The sheet includes an adhesive strip 310 with a water impervious polymer base 320. The adhesive layer also has an adhesive backing (not shown) made of nonstick or low stick material. The adhesive backing protects the adhesive layer during storage, but can be readily removed to expose the adhesive layer in preparation for use. For ease of use, the adhesive backing can include a tab for grasping and removal of the backing.

In use, the protective cover is applied to a user's limb of a person. The open end is placed about a limb of a person. The adhesive backing is removed and the adhesive is contacted with the skin of the user. The open end can be folded to bring opposing adhesive that is not contacting the skin in contact to form a seal, the sealed flap can be wrapped around the limb and secured with the adhesive tab. To provide an extra measure of protection from water leakage, the protective strip is wrapped around the seal formed between the limb and the protective cover.

In one or more embodiments, the protective cover can include a color indicator that changes color with increase in moisture. The color indicator would serve as an early indicator that the interior is wet. Contact indicator tapes such as are available from 3M are self-adhesive film/paper laminate constructions that change color from white to red when contacted by liquid water. They provide a fast, accurate and easy way to positively detect water intrusion. In other embodiments, the moisture detector can be applied directly to the inside of the protective barrier during manufacture of the bag.

In one or more embodiments, the protective cover can include an anti-microbial agent in protective cover interior. Casts and wound dressings are in constant contact with surfaces that are dirty and contain potentially harmful microorganisms. The damp environment of the bath is a good growth environment for such microorganisms and the use of an antimicrobial agent will help reduce proliferation of infections and diseases. Any antimicrobial agent used in the treatment of medical equipment and medical disposables can be used. The antimicrobial agent can be applied to the interior surface of the protective cover during manufacture.

As will be apparent to one of ordinary skill in the art from a reading of this disclosure, the disclosed subject matter can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

Figure 3A:
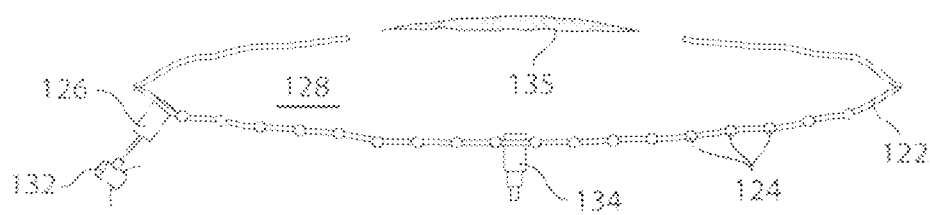
FIG. 3A represents various other embodiments of the water protective cover.

FIG. 3A depicts a further embodiment of the flexible sheet 122, shown in cross-section wherein a plurality of spaced apart ribs 124 are molded therein to provide structure and the ability of a sheet 122 to be spaced apart from a wound site. The ribs 124 may be of concentric orientation or linear and in parallel alignment with one another to act as rigidity inducing members to as to keep the sheet 122 from touching a wound. In yet a further embodiment shown also in FIG. 3A, an inlet port 126 may be arranged for receipt of a pressure inducing flexible-sheet-established wound enclosure chamber 128. The pressure chamber 128 in one preferred embodiment may be part of a system in which the chamber/sleeve may receive a generated inflation inducing pressure (gas filled) by insertion of and actuation of an inlet-port-piercing pressure canister 132. The object being spacing the flexible sheet 120/122 away from a wound site by controlled pressurization thereunder and/or with the sheet supporting ribs 124. A controlled fluid drain and/or pressure relief valve/duck bill valve 134 may be arranged through the sheet 122/124 to discharge any undesired fluids or excess vapors beyond that needed to keep the sheets 122/124 from touching a wound or treatment area 135. In an further embodiment with respect to the ribs 124, such ribs may be applied during sheet application, as a cutable, distortable, pinchable/foldable, site-dependent "applique" to the inner side or the outer side of a flexible sheet 122, so as to be more "personalized" as to configuration on a particular wound site 135. Such pressure canister 132 may be filled with medicaments and treatment fluids/gases for further wound treatment. In another embodiment, such ribs 124 may be of shape memory metal, such as for example, nitinol, which shapes itself according to temperature, which may be particularly desirable during a wound protecting/covering or a wound treating operation. Such a shape memory (nitinol) rib arrangement wound permit controlled spacing when a patient was showering or bathing to facilitate sheet 122/124 support away from a wound site.

What is claimed is:

1. A body part shielding protective cover assembly for use as a liquid barrier, comprising:
   a three-dimensional enclosure comprising a deformable front sheet and an attached back sheet, the front sheet having an applique of ribs thereon configured to keep the front sheet from touching the wound, said enclosure made of a flexible, liquid impervious material, the back sheet having an outer body-attachment-periphery in an interior portion of the back sheet and an inner wound-encircling periphery that defines a central, wound encircling opening; and
   an adhesive layer extending along an inner surface perimeter of the outer body attachment periphery of the back sheet for securing an outer periphery thereof onto the body part, wherein the inner wound-encircling periphery is positioned and sized so the assembly is arranged to cover and define an expandable three-dimensional wound shielding chamber.

2. The body part shielding protective cover assembly of claim 1, wherein the front and back sheets are sealed along their edges with a liquid impervious seal.

3. The body part shielding protective cover assembly of claim 1, wherein the front sheet is integral with the back sheet along two opposing sides, and the opposing edges are sealed with a liquid impervious seal.

4. The body part shielding protective cover assembly of claim 1, wherein the protective cover further comprises an adhesive backing disposed over the adhesive layer.

5. The body part shielding protective cover assembly of claim 1, further comprising a moisture indicator disposed in the interior of the enclosure.

6. The body part shielding protective cover assembly of claim 1, further comprising an antimicrobial agent disposed in the interior of the enclosure.

7. The body part shielding protective cover assembly of claim 1, having a front face which is distortably spaced apart from a back face of the body part shielding protective cover.

8. The body part shielding protective cover assembly of claim 1, wherein the body part shielding protective cover is body attachable.

9. The body part shielding protective cover assembly of claim 1, wherein the body part shielding protective cover is attachable to a joint of a body.

10. The body part shielding protective cover assembly of claim 1, wherein the cover comprises a gusset along at least one edge that joins the front and back sheets.

11. The body part shielding protective cover assembly as recited in claim 1, wherein the front sheet includes an inlet port for introduction of pressurized fluid into the expandable wound shielding chamber.

12. The body part shielding protective cover assembly as recited in claim 1, wherein the deformable ribbed-applique enhanced front sheet consists of a site-dependent patient-customizable applique.

13. The body part shielding protective cover assembly as recited in claim 1, wherein the applique has an array of shape memory material ribs thereon.

14. A three-dimensional body part shielding protective cover assembly for use as a liquid barrier, the cover assembly comprising an enclosure comprising a deformable, chamber reinforcing, front sheet and an attached back sheet, the front sheet having an applique of ribs thereon configured to keep the front sheet from touching the wound, said enclosure made of a flexible, liquid impervious material, the back sheet having an outermost body-attachment-periphery on a rear side of the back sheet and an inner periphery that defines a central, wound encircling opening; and an adhesive layer extending along an inner surface perimeter of an outer body periphery of the back sheet for securing an outer periphery thereof onto the body part, wherein the back sheet has an inner wound-encircling periphery which is positioned and sized so the assembly is arranged to cover and define an expandable wound shielding three-dimensional chamber, wherein the front and back sheets are sealed along their edges with a liquid impervious seal, and wherein the front sheet includes an inlet port to allow introduction of pressurized fluid into the expandable wound shielding chamber, wherein the applique consists of a site-dependent patient-customizable wound-contact-free applique, having an array of shape memory material ribs thereon.

\* \* \* \* \*